US006485479B1

(12) United States Patent
Knierbein

(10) Patent No.: US 6,485,479 B1
(45) Date of Patent: Nov. 26, 2002

(54) STERILE CONNECTOR

(75) Inventor: Bernd Knierbein, Neu-Anspach (DE)

(73) Assignee: Fresenius AG, Bad Homburg (DE)

( * ) Notice: Subject to any disclaimer, the term of this patent is extended or adjusted under 35 U.S.C. 154(b) by 0 days.

(21) Appl. No.: 09/426,851

(22) Filed: Oct. 26, 1999

Related U.S. Application Data

(63) Continuation of application No. PCT/EP98/02438, filed on Apr. 24, 1998.

(30) Foreign Application Priority Data

Apr. 26, 1997 (DE) ........................................ 197 17 765

(51) Int. Cl.$^{7}$ ............................................... A61B 19/00
(52) U.S. Cl. ....................................... 604/411; 604/244
(58) Field of Search ................................ 604/244, 256, 604/408, 415, 533, 411; 215/247, 250, 251; 220/265, 266, 271, 274; 222/81–83, 541.7

(56) References Cited

U.S. PATENT DOCUMENTS 3,364,930 A * 1/1968 Ryan .......................... 604/244
4,187,893 A 2/1980 Bujan
4,523,691 A 6/1985 Larkin et al.
4,547,900 A 10/1985 Larkin et al.
4,601,704 A 7/1986 Larkin

FOREIGN PATENT DOCUMENTS

GB 121 016 A 6/1983

OTHER PUBLICATIONS

International Search Report dated Oct. 09, 1998.

* cited by examiner

*Primary Examiner*—Anhtuan T. Nguyen
(74) *Attorney, Agent, or Firm*—Marshall, O'Toole, Gerstein, Murray & Borun

(57) ABSTRACT

A sterile connector is provided including a coupler, a protective cap, and a puncturable membrane film. The coupler has a tubular top with an upper edge defining an inwardly facing continuous shoulder, a mounting piece connected to the inwardly facing continuous shoulder adapted to sealably receive a plunge pin, a bottom insertable into a container having wall and sealable to the container wall, and a channel-like passage extending between the top and the bottom. The protective cap is attached to the tubular top of the coupler to seal the top, and has a lower edge connected to the inwardly facing continuous shoulder to define an annular rupture zone. The puncturable membrane film is sealed to the bottom of the coupler to close the channel-like passage. The sterile connector may be combined with a container, attached to the bottom of the coupler, to define an assembly.

10 Claims, 4 Drawing Sheets

STERILE CONNECTOR

CROSS-REFERENCE TO RELATED APPLICATION

This is a continuation of International Application No. PCT/EP98/02438 filed on Apr. 24, 1998, the entire disclosure of which is hereby incorporated by reference.

BACKGROUND OF THE INVENTION

1. Field of The Invention

The invention is directed to a sterile connector used to connect a line to a container filled with a medicinal liquid, and, in particular, a sterile connector with a removable protective cap used to connect a line to a container filled with a medicinal liquid.

2. Description of Related Technology

A film bag for medicinal liquids with a sterile connector for connection to a hose line is known from U.S. Pat. No. 4,201,406. The connector has a tube-like coupler which is sealed with a puncturable membrane. The membrane of the known connector is a plastic sheet, which is a one-piece component of the coupler. The hose line to be connected to the connector has a plunge pin, also referred to as a spike. The spike is surrounded concentrically by a tubular element that can be slid onto the coupler. The plunge pin is pushed into the coupler for connection of the hose line, so that the membrane is punctured and fluid connection is produced between the bag interior and the hose line connected to the spike.

The film bag can be sealed in sterile fashion with the known connector, but it has proven a drawback that the part of the coupler lying in front of the membrane is unprotected. A hazard therefore exists that germs will be introduced to the bag during puncturing of the membrane.

Connectors with releasable plastic closures, for example, screw caps, are also known. However, it has been shown in practice that during sterilization of connectors closed with screw caps in autoclaves, the hazard of leakage exists. O-rings made of silicone have therefore often been used, which seal any gap which may occur during sterilization. A disadvantage of this structure is that silicone rings are relatively expensive to produce in terms of the required purity of the material. Moreover, assembly of the connector is complicated because of the additional sealing elements required.

German Laid-Open Application 2458220 describes a sterile connector, comprising a tubular bottom and a tubular top, which encloses a puncturable membrane that is a one-piece component of the top. The bottom of the coupler is sealed to the bag, and the bag is filled through the opening of the bottom. After filling of the bag, the top is inserted into the bottom, the top and bottom mating via flanges that are sealed to each other. A tear-off closure cover is provided on the top of the coupler to cover the puncture opening.

European Patent Publication No. 732 114 describes a film bag for a liquid for intravenous feeding which has a connector applied to the film bag from the outside. The essentially tubular connector has a flange on its end on the bag side, which lies flatly on the outside of the bag film. In the known connector, the puncturable membrane is formed by the film of the bag itself. During insertion of the plunge pin into the connector, the bag film is punctured so that the fluid connection to the bag interior is produced. A sleeve nut that is screwed onto the tubular connector is provided to secure the plunge pin.

Film bags with a connector whose membrane consists of the bag film itself are generally filled aseptically, i.e., the bags are no longer sterilized in autoclaves after filling. An advantage of this film bag lies in the improved gas impermeability of the entire container, since the bag contents are fully closed by the gas-tight film. However, a shortcoming is that the connector, generally consisting of polyethylene, cannot be sealed to the outer layer of the bag film that generally consists of PET (polyethylene terephthalate), but only glued. This type of glue connection, however, generally leads to poorer production safety than a sealed joint.

A coupler for a flexible film bag that is sealed by a membrane is known from European Patent Publication No. 493 723. The membrane can be punctured with a plunge pin integrated in the protective cap. It is proposed for improvement of the gas barrier that the membrane be a film, which is sealed to the bottom of the coupler.

It is an object of the present invention is to devise a connector suitable for sterilization in autoclaves that offers high safety against contamination of the container, is easily handled and can be produced in large numbers cost-effectively.

SUMMARY OF THE INVENTION

According to an aspect of the invention, a sterile connector is provided including a coupler, a protective cap, and a puncturable membrane film. The coupler has a tubular top with an upper edge defining an inwardly facing continuous shoulder, and a mounting piece connected to the inwardly facing continuous shoulder and adapted to sealably receive a plunge pin. The coupler also has a bottom insertable into a container having wall and sealable to the container wall. The coupler further includes a channel-like passage extending between the top and the bottom. The protective cap is attached to the tubular top of the coupler to seal the top, and has a lower edge connected to the continuous shoulder to define an annular rupture zone. The puncturable membrane film is sealed to the bottom of the coupler to close the channel-like passage.

According to another aspect of the invention, a container may be attached to the bottom of the coupler of the connector to define an assembly.

BRIEF DESCRIPTION OF THE DRAWINGS

An embodiment of the invention is further explained below with reference to the drawings, in which.

DETAILED DESCRIPTION OF THE PREFERRED EMBODIMENT

Figure 1:
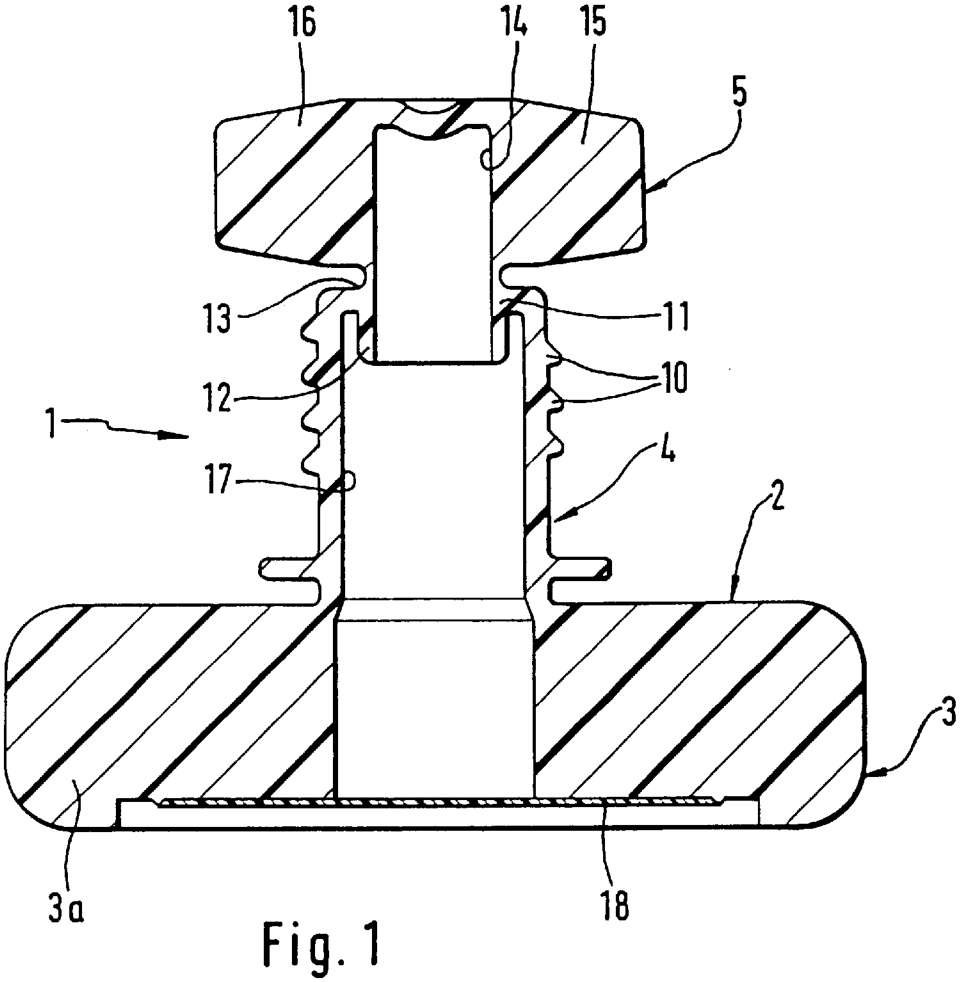
FIG. 1 is a cross-sectional view of a connector according to an embodiment of the present invention.
Figure 2:
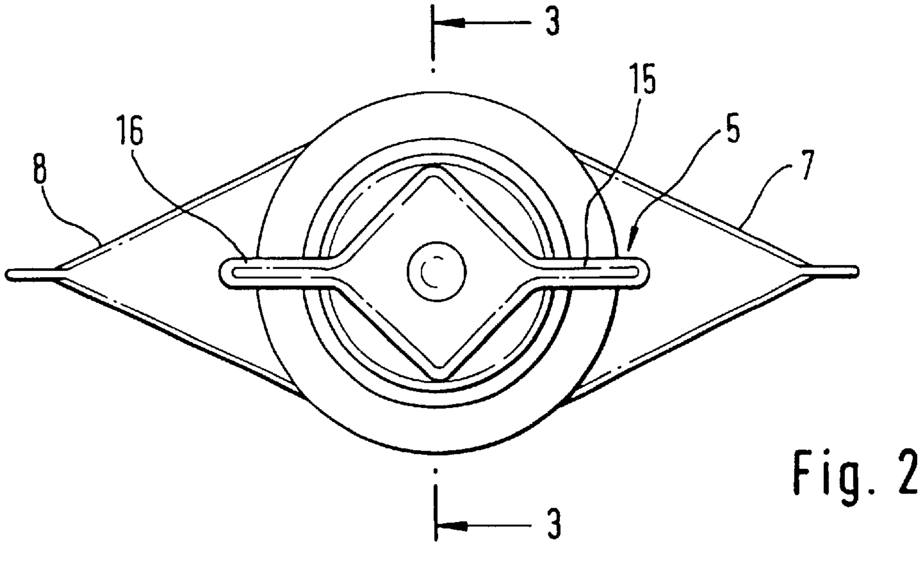
FIG. 2 is a top view of the connector of FIG. 1.
Figure 3:
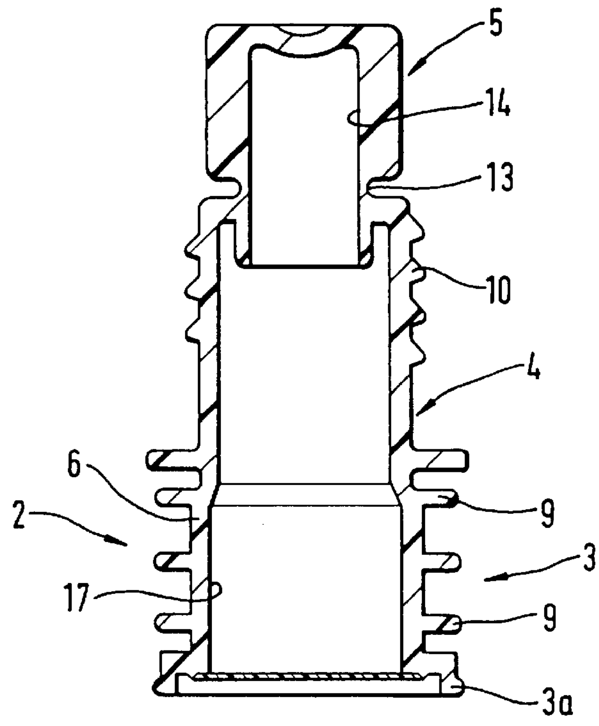
FIG. 3 is a cross-sectional view of the connector of FIG. 1 in the direction of line 3—3 in FIG. 2.

A connector 1 according to an embodiment of the invention is shown in FIG. 1. The connector 1 includes a coupler 2 with a bottom 3 shaped like a boat and a tubular top 4, and a protective cap 5.

The bottom 3 of the coupler 2 has a tubular section 6 provided with two radially protruding wing-like shoulders 7, 8 that lie in one plane. The wing-like shoulders 7, 8 carry ribs 9 that taper to a point on the ends of the shoulders 7, 8. The bottom 3 is sealable to the inside of the bag film of suitable film bags for medicinal liquids.

The tubular top 4 of the coupler, which is connected to the bottom 3, is provided with an outside threading 10 for screwing-on of a sleeve nut. The tubular top 4 has a continuous inwardly facing shoulder 11 on its upper edge, to which a mounting piece 12 is attached for accommodation of a plunge pin in sealed fashion. The mounting piece 12 has a rectangular cross-section with rounded corners, corresponding to the cross-section of the plunge pin, to prevent rotation of the plunge pin.

The protective cap 5 is attached to and seals the tubular top 4 of the coupler 2 at one end. In particular, a lower edge of the protective cap 5, which has a relatively small diameter, is connected to the inwardly facing shoulder 11 of the tubular top 4 of the coupler 2 to define an annular rupture zone 13. It is advantageous if the protective cap 5 has a relatively small diameter and the wall of the protective cap 5 is designed relatively thin in the region of the annular rupture zone 13. The protective cap 5 also has a cylindrical recess 14.

The cap 5 and the coupler 2 are preferably connected as a one-piece structure. With cap 5 and the coupler 2 preferably formed as a one-piece structure, additional manufacturing processes after sterilization, like drying, disinfection, screwing-on, etc., can be eliminated. This is a particular advantage in manufacturing flexible packages, since the expense for additional manufacturing steps after sterilization here is particularly high. It is also advantageous that no elastomeric components, like silicone O-rings, are required for tight closure of the connector 1, these additional items involving greater manufacturing and assembly costs and requiring that grade purity of the entire connector arrangement is guaranteed.

The protective cap 5 is designed as a tear-off part. To this end, the protective cap 5 is provided with two wings 15, 16 extending in the radial direction, so that the wings 15, 16 can be easily grasped and the required torque easily applied to the cap 5 to tear it off. The protective cap 5 thus configured so that it can be easily opened by untrained or older persons, for example, in the home care field.

To open the connector 1 before introduction of a plunge pin into the coupler 2, the protective cap 5 is rotated around its longitudinal axis so that the wall ruptures along the annular rupture zone 13. Because the tubular section 4 of the coupler 2 is only exposed thereafter, there is a limited hazard that germs will be introduced to an associated container during introduction of a plunge pin into the opened connector 1. It will be recognized that the protective cap 5 serves not only for bacterial protection of the puncture site, but also represents an original closure.

A channel-like passage 17 is formed in the connector 1, and is covered and sealed with a puncturable membrane film 18. Preferably, the membrane film 18 has an oxygen permeability of less than 1 $cm^3/m^2$ d bar. The film material may be a gas-tight plastic, like EVOH (ethylene-vinyl alcohol copolymers), or coatings of film substrates, like $SiO_x$ or $AMO_x$. The film 18 is sealed by welding to the bottom of the coupler bottom 3. The film 18 preferably extends almost over the entire lower surface of the coupler bottom 3 and is enclosed by a continuous edge 3*a*.

Production of the connector 1 according to the invention relative to connectors with a one-piece membrane that has a tear-off protective cap, may be simplified by manufacturing the coupler 2 and cap 5 using an injection molding process without cavities. Preferably, the coupler 2 and cap 5 are made of polypropylene, so that known bag films having a sealing layer on their inside made of the same material can be welded to the connector 1 without difficulty. The welded assembly of the connector 1 and the bag would have a melting point higher than the sterilization temperature and can, therefore, be sterilized in autoclaves.

The membrane film 18 can be welded to the bottom 3 of the coupler 2 directly after injection molding of the coupler 2 and the cap 5 in the sterile state, so that the space in front of the membrane is tightly sealed. For a case in which welding only occurs later, under nonsterile conditions, a water drop can be introduced to the channel-like passage 17 between the membrane film 18 and the cap 5, which evaporates during sterilization and thus permits reliable and safe sterilization of the cavity.

Figure 4:
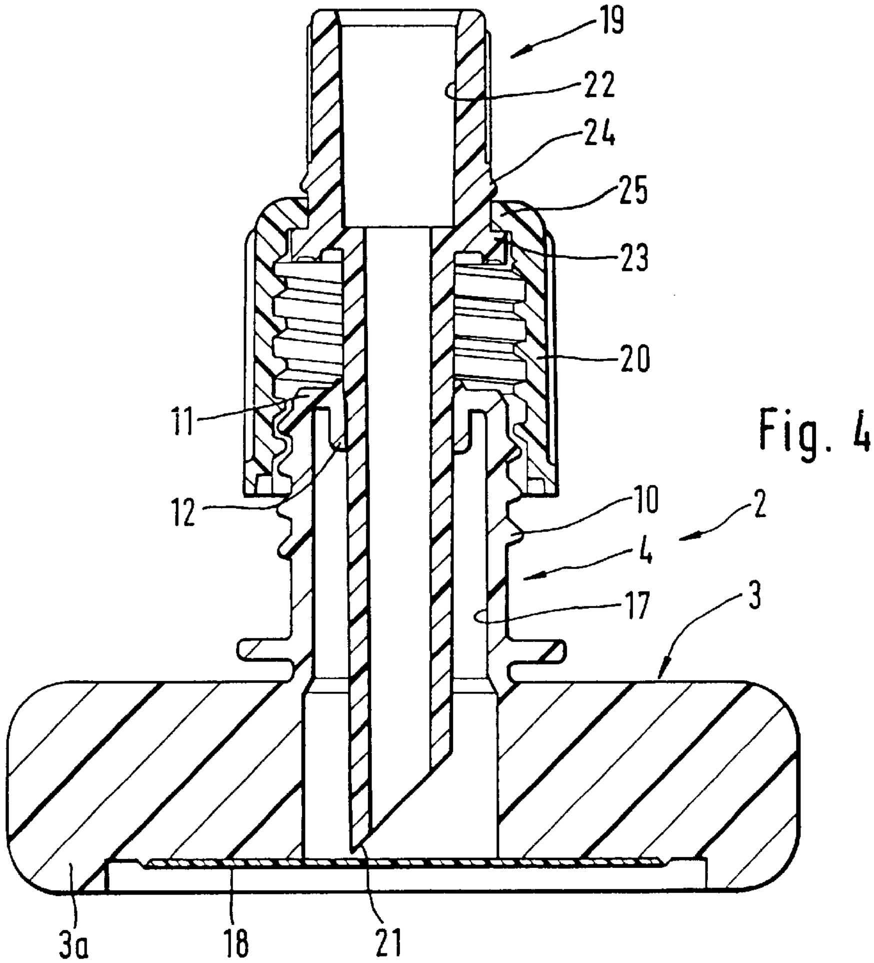
FIG. 4 is a cross-sectional view of the connector of FIG. 1 in combination with a plunge pin and a sleeve nut, the plunge pin being inserted into the coupler without puncturing the film membrane.

FIG. 4 shows an assembly including the connector 1 and a plunge pin or spike 19 with a externally ribbed sleeve nut 20. The tubular plunge pin 19 has a tip 21 on one end, and can be connected on its other end to a plastic tube of a hose line (not shown) which is pushed into an upper shoulder 22 of plunge pin 19. The plunge pin 19 is sealed relative to the inner mounting piece 12 of the coupler top 4 in an inserted position.

The plunge pin 19 has a continuous edge 23 beneath the shoulder 22, which edge 23 is supported on an upper edge of the coupler top 4 with the pin 19 inserted into the connector 1. The sleeve nut 20, which is seated on the edge 23, is secured against loss by a continuous cross piece 24 on the shoulder 22 of the plunge pin 19 on the hose side.

Figure 5:
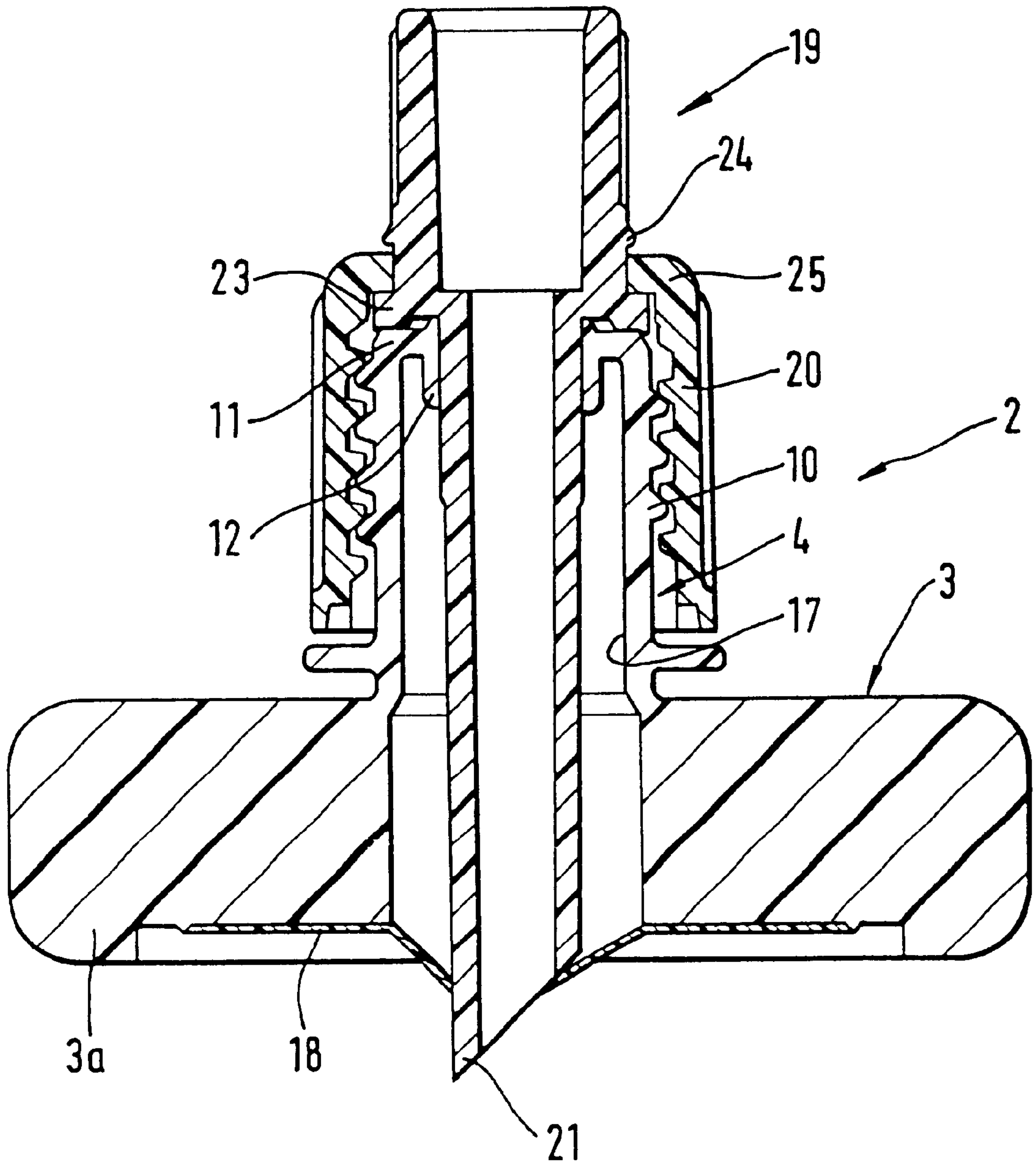
FIG. 5 is a cross-sectional view of the combination of connector, plunge pin and sleeve nut of FIG. 4 with the plunge pin puncturing the membrane film.

When the sleeve nut 20 is screwed on, the plunge pin 19 is moved in the axial direction toward membrane film 18, puncturing it. FIG. 5 shows the arrangement with the punctured membrane film 18 and the screwed-on sleeve nut 20. The continuous sleeve 23 on the outside of the plunge pin 19 is thus clamped between the tubular top 4 and an inwardly protruding edge 25 of the sleeve nut 20. The tip 21 of the plunge pin 19 extends through the membrane film 18 into the bag interior.

The connector 1 according to the invention can find application in medical packaging units of different design. A preferred area of application is with film bags filled with a medicinal liquid, especially a liquid for intravenous feeding.

Figure 6:
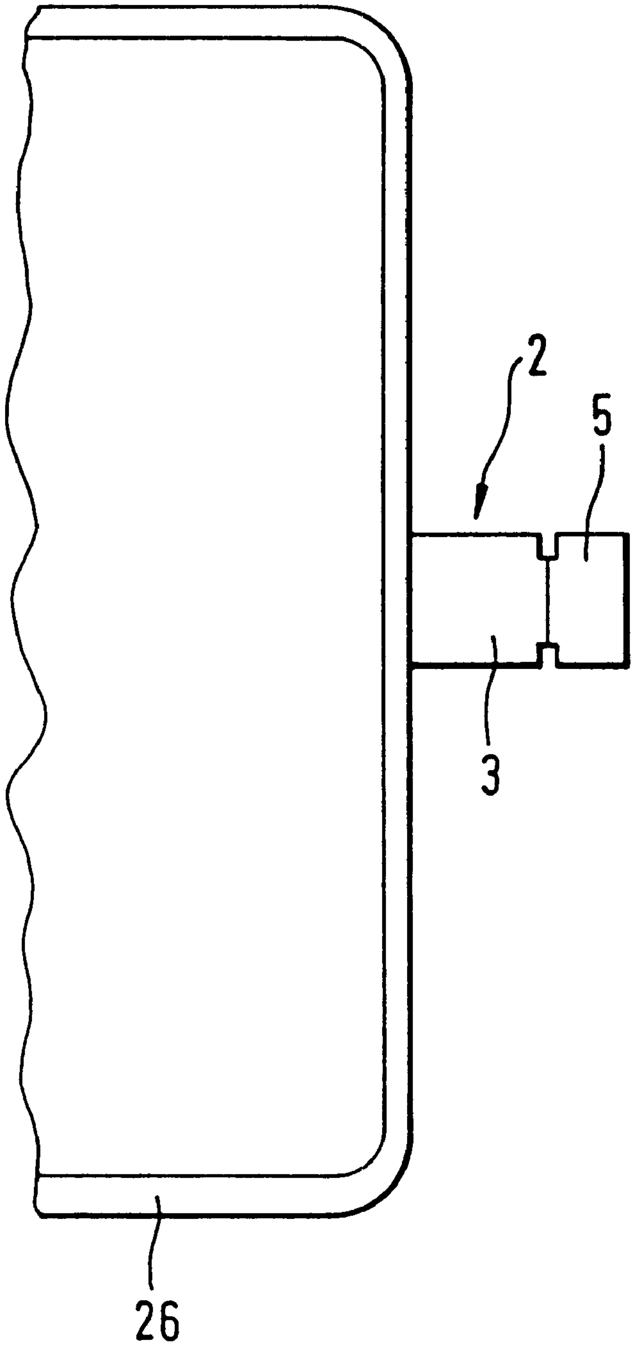
FIG. 6 is a schematic view of the connector of FIG. 1 in combination with a film bag container.

FIG. 6 shows a film bag filled with a medicinal liquid for intravenous feeding. The bag consists of two superimposed plastic films 26 sealed together on their edges, which have an inner sealing layer of polypropylene and are sealed by welding to the bottom 3 of the coupler 2 of the connector 1. The coupler 2, therefore, need not be attached to the outside of the bag, but instead the coupler can be welded to the inside, as is the case in known connectors whose membrane is a one-piece component of the coupler. Production safety is improved with this type of welded joint.

In use, after turning the protective cap 5, a plunge pin 19 connected to a hose or line may be inserted into the connector 1 and secured thereto using the sleeve nut 20, so that the bag interior and the hose or line are in fluid communication.

Other aspects, objects, and advantages of the present invention will be obtained from a study of the specification, drawings and appended claims.

I claim:

1. A sterile connector comprising:

a coupler having a tubular top with an upper edge defining an inwardly facing continuous shoulder, a mounting piece connected to the inwardly facing continuous shoulder and adapted to sealably receive a plunge pin, a bottom insertable into a container having wall and sealable to an interior container wall, and a channel-like passage extending between the top and the bottom;

a protective cap attached to the tubular top of the coupler to seal the top and having a lower edge connected to the inwardly facing continuous shoulder to define an annular rupture zone; and a puncturable membrane film sealed to the bottom of the coupler to close the channel-like passage.

2. The sterile connector according to claim 1, wherein the puncturable membrane film has an oxygen barrier of less than 1 $cm^3/m^2$ d bar.

3. The sterile connector according to claim 2, wherein the coupler and the protective cap comprise polypropylene.

4. The sterile connector according to claim 3, wherein the bottom has an edge which encloses the puncturable membrane film.

5. The sterile connector according to claim 4, wherein the tubular top has an external threading to screwably receive a threaded sleeve nut.

6. The sterile connector according to claim 1, wherein the protective cap further includes a manual gripping element for gripping the protective cap to break the annular rupture zone and remove the cap from the coupler.

7. An assembly comprising:

a sterile connector including (i) a coupler having a tubular top with an upper edge defining an inwardly facing continuous shoulder, a mounting piece connected to the inwardly facing continuous shoulder and adapted to sealably receive a plunge pin, a bottom, and a channel-like passage extending between the top and the bottom, (ii) a protective cap attached to the tubular top of the coupler to seal the top and having a lower edge connected to the continuous shoulder to define an annular rupture zone, and (iii) a puncturable membrane film sealed to the bottom of the coupler to close the channel-like passage; and a container having a wall defining an opening therethrough, the bottom of the coupler inserted into the opening of the container wall and sealably connected to an interior container wall.

8. The assembly according to claim 7, wherein the container has an inner sealing layer, and the coupler, the cap and the inner sealing layer comprise polypropylene.

9. The assembly according to claim 7, wherein the container comprises a film bag filled with a medicinal liquid.

10. The assembly according to claim 7, wherein the sterile connector protective cap includes a manual gripping element for gripping the protective cap to break the annular rupture zone and remove the protective cap from the coupler.

* * * * *